US006949493B1

(12) United States Patent
Zhang et al.

(10) Patent No.: US 6,949,493 B1
(45) Date of Patent: Sep. 27, 2005

(54) SOAP BARS COMPRISING SYNERGESTICALLY HIGH LEVELS OF BOTH FREE FATTY ACID AND FILLER

(75) Inventors: Xiaodong Zhang, Livingston, NJ (US); Vivek Subramanian, Livingston, NJ (US); Pravin Shah, Rutherford, NJ (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 0 days.

(21) Appl. No.: 10/849,408

(22) Filed: May 19, 2004

(51) Int. Cl.[7] .......... A61K 7/50
(52) U.S. Cl. .......... 510/141; 510/151; 510/152; 510/153; 510/154; 510/155
(58) Field of Search .......... 510/141, 152, 510/153, 154, 155

(56) References Cited

U.S. PATENT DOCUMENTS

| | | | | |
|---|---|---|---|---|
| 3,576,749 A | | 4/1971 | Megson et al. | |
| 5,952,289 A | * | 9/1999 | Wise et al. | 510/450 |
| 6,218,347 B1 | * | 4/2001 | Rau et al. | 510/151 |
| 6,242,399 B1 | * | 6/2001 | Chambers et al. | 510/154 |
| 6,384,000 B1 | * | 5/2002 | McFann et al. | 510/152 |
| 6,600,699 B2 | * | 7/2003 | Miyazaki | 369/30.15 |
| 2002/0045555 A1 | | 4/2002 | Andreas et al. | |

OTHER PUBLICATIONS

Copending U.S. Appl. No. 10/849,627, filed May 19, 2004, Tsaur et al., Personal Product Liquid Cleansers Stabilized with Starch Structuring System.
Copending U.S. Appl. No. 10/849,100, filed May 19, 2004, Tsaur et al., Personal Product Liquid Cleansers Combined Fatty Acid and Water Soluble or Water Swellable Starch Structuring System.

* cited by examiner

*Primary Examiner*—Necholus Ogden
(74) *Attorney, Agent, or Firm*—Ronald A. Koatz

(57) ABSTRACT

The present invention comprises novel bar compositions comprising relatively high levels of soap and of filler while maintaining good user properties.

5 Claims, 1 Drawing Sheet

SOAP BARS COMPRISING SYNERGESTICALLY HIGH LEVELS OF BOTH FREE FATTY ACID AND FILLER

FIELD OF THE INVENTION

The present invention relates to bar soaps, preferably fatty acid soap based bars which have relatively large amounts of both free fatty acid (e.g., measured as a ratio relative to amount of soap) and of filler (e.g., also as a ratio relative to amount of soap).

BACKGROUND

The use of either free fatty acid or of filler, individually, in a fatty acid soap bar is known in the art.

Thus, for example, free fatty acid has been used in soap bar compositions. The addition of such free fatty acid is known as "superfatting" and superfat may be used to make a bar with enhanced user properties like enhanced lather and/or bar feel. However, it is known that, if too much free fatty acid is used in the bar, the bar may be too soft for structuring purposes such that a bar may not be processed at all and, if it is, may be extremely soft. In typical soap bars, the ratio of free fatty acid to total fatty matter (TFM) is not greater than 0.06. TFM is combination of free fatty acid and fatty acid soap.

The use of filler materials (e.g., organic particles, polymers, wax, sugar, etc.) in soap bar compositions is also known. The use of too much filler is also generally considered undesirable because high filler can cause loss of bar integrity (crumbly bars). Again, it is typically found that the ratio of filler to TFM in a soap bar is not greater than 0.2.

Thus, if either filler or free fatty acid (FFA) alone is used in excess (very high ratios compared to soap), this can be very detrimental to processing and/or bar properties.

Unexpectedly, however, applicants have found that when high ratios of free fatty acid and of filler are used simultaneously, the use of one cancels out the deficiencies of the other such that, synergistically, they create a better overall bar. Thus, for example, the high degree of softness that would normally be expected from using high ratio of FFA to TFM is firmed up by the filler which is used. Moreover, the filler can now be used in higher ratios without affecting bar integrity because it is compensating for the softness caused by the free fatty acid; and, at the same time, the filler brings sensory benefits (e.g., creamier lather).

U.S. Pat. No. 3,576,749 to Megson discloses a soap bar with 2 to 15% free fatty acid. There is no disclosure of what happens to bar properties (e.g., increased softness) if free fatty acid is used in high amounts (for example at above 10%) and where there is no filler to compensate for such softness. In general, there is no disclosure of the combination of free fatty acid and filler, both used at in defined minimum ratios claimed in the subject invention, or of the synergistic effect unexpectedly allowing both to be used in such high amounts.

U.S. Patent Application Publication 2002/0045555 discloses bars containing talc and fatty acid. Again, however, there is no teaching or disclosure that levels of filler (e.g. talc) and free fatty acid (defined as ratio to total soap) can be high; nor is there a disclosure that there is an advantage (e.g., enhancing both foaming and tactile sensory properties) in doing so.

Unexpectedly, applicants have now found that the filler and free fatty acid can be combined in specifically claimed ratios relative to soap to obtain advantages.

BRIEF DESCRIPTION OF THE INVENTION

The subject invention relates to soaps:

(1) wherein the ratio of free fatty acid to TFM is greater than or equal to 0.06; and (2) wherein the ratio of filler to TFM is greater than or equal to 0.2.

Bars with such ratios of ingredients are processable, are not too soft (as measured, for example, by yield stress) and have good lather.

In a second embodiment of the invention the reference relates to a method for enhancing both foaming and tactile sensory properties while maintaining bar processability which method involves using soap/free fatty acid/filler bars:

(1) where ratio of fatty acid to TFM is greater than or equal to 0.06; and (2) the ratio of filler to TFM is greater or equal to 0.2.

These and other aspects, features and advantages will become apparent to those of ordinary skill in the art from a reading of the following detailed description and the appended claims. For the avoidance of doubt, any feature of one aspect of the present invention may be utilized in any other aspect of the invention. It is noted that the examples given in the description below are intended to clarify the invention and are not intended to limit the invention to those examples per se. Other than in the experimental examples, or where otherwise indicated, all numbers expressing quantities of ingredients or reaction conditions used herein are to be understood as modified in all instances by the term "about". Similarly, all percentages are weight/weight percentages of the total composition unless otherwise indicated. Numerical ranges expressed in the format "from x to y" are understood to include x and y. When for a specific feature multiple preferred ranges are described in the format "from x to y", it is understood that all ranges combining the different endpoints are also contemplated. Where the term "comprising" is used in the specification or claims, it is not intended to exclude any terms, steps or features not specifically recited. All temperatures are in degrees Celsius (° C.) unless specified otherwise. All measurements are in SI units unless specified otherwise. All documents cited are—in relevant part—incorporated herein by reference.

Figure 1:
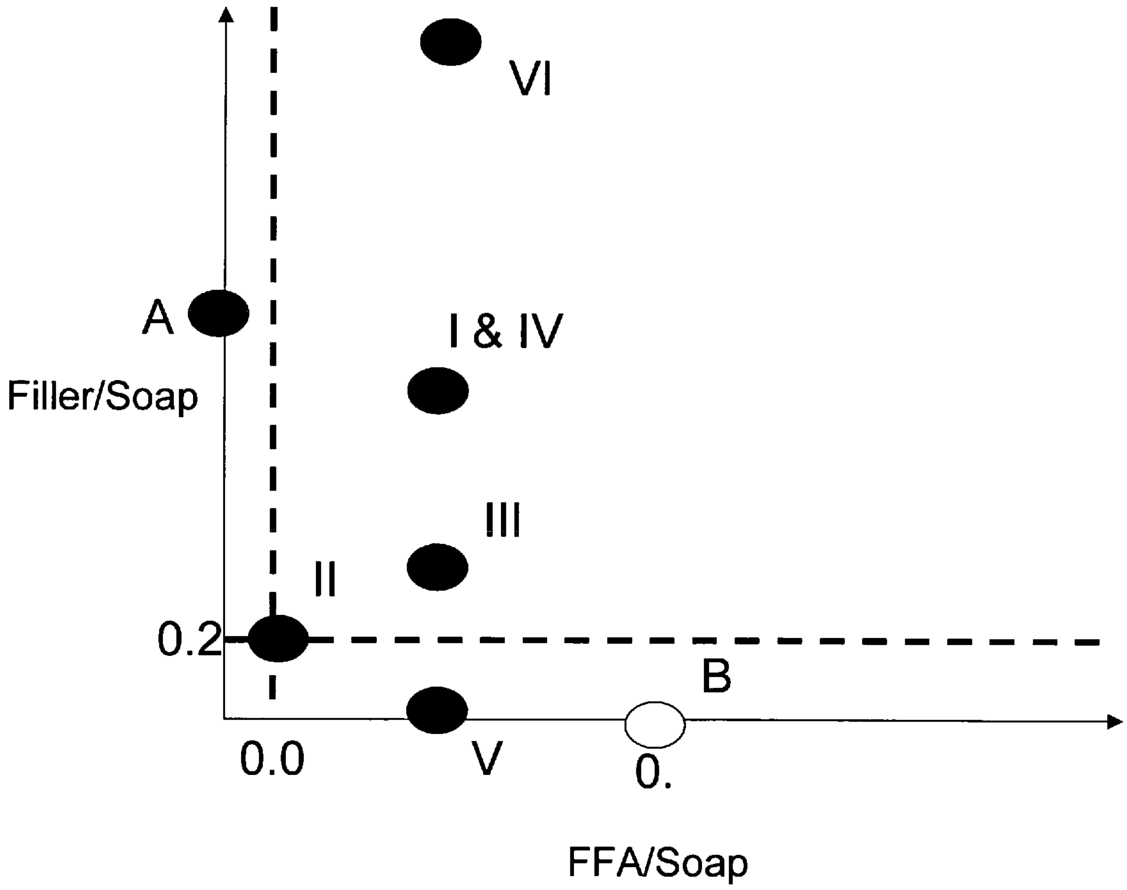
FIG. 1 is a schematic of region in which synergies of the invention occur.

Specifically at points where there is filler, but no free fatty acid, or free fatty acid but no filler (A & V), either the lather properties or the yield stress of the billet is low. At other points, a bar with yield stress above 150 kPa is obtained in conjunction with superior lather attributes as described in the examples.

DETAILED DESCRIPTION OF THE INVENTION

In one embodiment, the present invention relates to soap/free fatty acid bars which contain both relatively high ratios of free fatty acid (normally causing excessive softness) to soap, and a relatively high ratios of filler (normally causing cracking and lack of processability) to soap, yet which filler and FFA act synergistically to produce bars with good lather (i.e., at least 18 ml, preferably at least 20, more preferably at least 25 by lather volume test described in protocol) which process well (yield stress of at least 150, as measured by the cheese wire test described in protocol), all with little or no cracking.

Specifically, in this embodiment, the invention relates to bars comprising:

(1) 20 to 75%, preferably 30 to 60% by wt. fatty acid soaps;

(2) 3 to 30%, preferably 4 to 25% by wt. free fatty acid;

(3) 20 to 60%, preferably 25 to 55% by wt. filler materials; and (4) 1% to 15% water, wherein the ratio of free fatty acid to TFM is greater than or equal to 0.06; and wherein the ratio of filler to TFM (free fatty acid+soap) is greater to or equal to 0.2;

wherein said bar has lather of at least 18, more preferably at least 20 ml as measured by lather volume test; and wherein said bar has a yield stress of at least 150, as measured by cheese wire test.

In a second embodiment of the invention the invention relates to a method of enhancing foam (foam of at least 18, preferably at least 20 ml.) and/or tactile sensory properties while maintaining bar processing (yield stress above 150 by cheese wire test), which method comprises using soap bar with ratios as defined.

In another embodiment, the bars of the invention (with ratios as defined) have, relative to bars which don't satisfy both ratio requirements, an improvement of at least 1% in at least lather volume (measured in ml by lather volume test) or opacity (measured in pixel intensity).

The bar is defined with more particularly below.

Bars of the invention comprise 20% to 75% by wt., preferably 30% to 60% soap.

The term "soap" is used here in its popular sense, i.e., the alkali metal or alkanol ammonium salts of aliphatic alkane- or alkene monocarboxylic acids. Sodium, potassium, mono-, di and tri-ethanol ammonium cations, or combinations thereof, are suitable for purposes of this invention. In general, sodium soaps are used in the compositions of this invention, but from about 1% to about 25% of the soap may be potassium soaps. The soaps useful herein are the well known alkali metal salts of natural or synthetic aliphatic (alkanoic or alkenoic) acids having about 12 to 22 carbon atoms, preferably about 12 to about 18 carbon atoms. They may be described as alkali metal carboxylates of acrylic hydrocarbons having about 12 to about 22 carbon atoms.

Soaps having the fatty acid distribution of coconut oil may provide the lower end of the broad molecular weight range. Those soaps having the fatty acid distribution of peanut or rapeseed oil, or their hydrogenated derivatives, may provide the upper end of the broad molecular weight range.

It is preferred to use soaps having the fatty acid distribution of coconut oil or tallow, or mixtures thereof, since these are among the more readily available fats. The proportion of fatty acids having at least 12 carbon atoms in coconut oil soap is about 65%. The proportion will be greater when mixtures of coconut oil and fats such as tallow, palm oil or non-tropical nut oils or fats are used, wherein the principle chain lengths are $C_{16}$ and higher. Preferred soap for use in the compositions of this invention has at least about 85% fatty acids having about 12–18 carbon atoms.

Coconut oil employed for the soap may be substituted in whole or in part by other "high-lauric" oils, that is, oils or fats wherein at least 50% of the total fatty acids are composed of lauric or myristic acids and mixtures thereof. These oils are general exemplified by the tropical nut oils of the coconut oil class. For instance, they include: palm kernel oil, babassu oil, ouricuri oil, tucum oil, cohune nut oil, murumuru oil, jaboty kernel oil, khakan kernel oil, dika nut oil, and ucuhuba butter.

A preferred soap is a mixture of about 30% to about 35% coconut oil and about 60% to about 65% tallow. These mixtures contain about 95% fatty acids having about 12 to about 18 carbon atoms. The soap may be prepared from coconut oil in which case the fatty acid content is about 70% of $C_{12}$–$C_{18}$ chain length.

The soaps may contain unsaturation in accordance with commercially acceptable standards. Excessive unsaturation is normally avoided.

Soaps may be made by the classic kettle boiling process or modern continuous soap manufacturing processes wherein natural fats and oils such as tallow or coconut oil or their equivalents are saponified with an alkali metal hydroxide using procedures well known to those skilled in the art. Alternatively, the soaps may be made by neutralizing fatty acids, such as lauric ($C_{12}$), myristic ($C_{14}$), palmitic ($C_{16}$) or stearic ($C_{18}$) acids with an alkali metal hydroxide or carbonate.

The bar may optionally contain 0 to 10% by wt. synthetic, non-soap surfactant which surfactant may be selected from the group consisting of anionic, nonionic, amphoteric, and cationic surfactants, although it should be understood that bars are predominantly soap bars and levels of synthetic, if any, are minimal.

Bars of the invention comprise 3% to 30% by wt., preferably 4% to 25% by wt. free fatty acids. As indicated, there must be sufficient free fatty acid such that ratio of free fatty acid to total fatty matter (includes soap plus free fatty acid) is equal or greater than 0.06, preferably greater than 0.08, more preferably greater than 0.1.

Generally (e.g., in absence of amount of filler used in the subject invention), such amounts of free fatty acid will create bars which foam well, but which are too soft (e.g., yield stress <100). According to our invention, bars of the invention will have foam value of at least 18, yet not be too soft and process well (e.g., yield stress values above 150 kPa).

Bars of the invention will generally comprise large amounts of filler. Typically they will comprise about 20% to 60% filler, preferably 25% to 55% by wt. filler.

Fillers relate to all inert organic or inorganic materials which can be added to conventional soap bars including clays, silica, calcium carbonate, starch, sugar and mixtures thereof.

Preferred fillers include talc, clays, silica and mixtures thereof.

According to the invention, as noted, ratio of free fatty acid to TFM is 0.06 or greater. Specifically it may range from 0.06 to 0.4, preferably 0.06 to 0.2.

Bars of the invention further will have ratio of filler to TFM of $\geqq$0.2 to 4, preferably 0.25 to 3.

Bars of the invention will have lather of at least 18 ml, as measured by the lather volume method defined in further detail in protocol section.

Bars of the invention will process well defined as having a yield stress greater than 150 kPa as measured using cheesewire with a 200 g wt attached.

There are two kinds of processing methods used for the examples shown below. In the first method, a small 15 g intensive shear mixer was used to mix the materials which were then pressed into a tablet using a hydraulic manual Carver press. The tablets were evaluated for user properties like lather. In the second method, soap bars were processed using the conventional mixing, milling, plodding and stamping route to estimate processability.

EXAMPLES

Protocol

Lather Volume and Opacity Test

The tablets and/or bars were wetted by rubbing 10 times in tap water at 40° C. They were then equilibrated for 5 minutes. The tablets or bars were then taken in one palm, wetted in running water and rubbed on the other 10 times. The lather was collected into the palm and then creamed a further 20 times. The density (gas fraction) of the lather was estimated by weighing and the total volume (measured in ml) was determined using this information along with the total weight of the foam generated. Opacity of the foam was estimated by filling a small petri dish with the foam and taking a photograph under high intensity halogen lights to eliminate variations in illumination. The image was then estimated for average pixel intensity using the commercially available Scion image software.

Yield stress was measured using a the cheese wire test, with a cheese-wire of diameter 0.5 mm and a 200 gm weight.

Examples 1–4 and Comparatives A & B

In order to show the synergistic affect of filler and FFA, applicants prepared the following tablets using the 15 g mixer and Carver press. In these examples, in the first row 65/35 refers to the ratio of tallow to palm kernel oil soap in the bar. The following formulations were prepared:

| Ingredients | Example 1 | Comparative A (No FFA) | Comparative B (No Filler) | Example 2 | Example 3 | Example 4 |
|---|---|---|---|---|---|---|
| 65/35 | 7.65 | 7.5 | 10.5 | 11.8 | 9.825 | 7.65 |
| Talc | 6.0 | 7.5 | 0 | 2.5 | 3.45 | 0 |
| Silica | 0 | 0 | 0 | 0 | 0 | 6.0 |
| FFA | 1.35 | 0 | 4.5 | 0.7 | 1.725 | 1.35 |
| Filler/Total Soap | 0.67 | 1 | 0 | 0.2 | 0.3 | 0.67 |
| FFA/Total Soap | 0.15 | 0 | 0.3 | 0.06 | 0.15 | 0.15 |

Further, volume and opacity results are reported as follows:

| | 1 | Comp. A | Comp. B | 2 | 3 | 4 | 85/15 |
|---|---|---|---|---|---|---|---|
| Lather Volume (ml) | 37.3 | 15.2 | 17.2 | 26.4 | 27.8 | 19.6 | 17.8 |
| Opacity | 120.5 | 189.6 | 128.76 | 191.1 | 172.97 | 130.13 | 135.3 |

85/15 is the standard soap bar where the numbers 85 and 15 refer to the ratio of tallow to coconut soap in the bar. The volume numbers for A and B are comparable to the control suggesting that filler and FFA alone are not enough for good lather. However, 1, 2 and 3 show a lather volume of almost two times compared to the control showing the synergistic effect of FFA and filler. The whiteness of the lather is an estimate of the bubble size; the smaller the latter, the whiter the foam appears to be. A whiter foam is often regarded by consumers as creamy. The results show that whiteness of A, 2 and 3 are very high compared to the control, most likely due to fine bubble size. Since A is low in volume, 2 and 3, which have high ratios of both filler and FFA are the only formulations which give that largest lather volume with small bubbles. Comparing 1 and 4 suggests that some fillers like talc may be better than others, like silica, for lather volume.

The following fully formulated bars show the yield stress values of the billet at 40° C. A yield stress of at least 150 kPa (kilopascals) is considered acceptable.

| Ingredients | Comparative C | Example 5 | 85/15 (Control) |
|---|---|---|---|
| 65/35 | 0 | 27.58 | 0 |
| 85/15 | 76.5 | 0 | 86.0 |
| Talc | 0 | 60 | 0 |
| FFA | 10 | 3.67 | 0 |
| water | 12.5 | 6 | 12 |
| Perfume | 1.0 | 1.75 | 1 |
| Filler/Total Soap | 0 | 2.2 | 0 |
| FFA/Total Soap | 0.12 | 0.12 | 0 |
| Yield Stress (kPa) | 90 | 294 | 294 |

The above examples show that Comparative which has a high ratio of FFA, but no filler, has an unacceptably low yield stress, whereas Example 5, which has a high ratio of both FFA and of filler, has the same yield stress as the control and is very easy to process.

What is claimed is:

1. Bar composition comprising:

(a) 20 to 75% by wt. fatty acid soap;

(b) 3 to 30% free fatty acid;

(c) 20 to 60% filler; and (d) 1 to 15% water;

wherein the ratio of fatty acid to total soap is greater than or equal to 0.15; and wherein the ratio of filler to total soap is greater than or equal to 0.3;

wherein bars have lather of at least 18 mls as measured by defined lather volume test; and wherein said bar has a yield stress of at least 150 kPa as measured by cheesewire test using 0.5 mm cheesewire diameter and 200 gram wt.

2. A bar composition according to claim 1 having 3 to 30% fatty acid soap.

3. A bar composition according to claim 1, wherein said filler is selected from talc, clay, silica and mixtures thereof.

4. A bar according to claim 1, having lather of at least 20 mls.

5. A bar according to claim 1 having an increase of at least 1% in at least lather (measured in ml) or opacity (measured in pixel intensity) relative to a bar which does not have both a ratio of fatty acid to soap greater than or equal to 0.15 and ratio of filler to soap greater than or equal to 0.3.

* * * * *